(12) United States Patent
Vasconcelos Araujo et al.

(10) Patent No.: US 11,996,699 B2
(45) Date of Patent: May 28, 2024

(54) RECEIVING UNIT, TRANSMISSION UNIT, POWER TRANSMISSION SYSTEM AND METHOD FOR WIRELESS POWER TRANSMISSION

(71) Applicant: KARDION GMBH, Stuttgart (DE)

(72) Inventors: Samuel Vasconcelos Araujo, Esslingen (DE); Michael Jiptner, Besigheim (DE)

(73) Assignee: Kardion Gmbh, Stuttgart (DE)

( * ) Notice: Subject to any disclaimer, the term of this patent is extended or adjusted under 35 U.S.C. 154(b) by 752 days.

(21) Appl. No.: 17/051,405

(22) PCT Filed: May 2, 2019

(86) PCT No.: PCT/EP2019/061320
§ 371 (c)(1),
(2) Date: Jul. 26, 2021

(87) PCT Pub. No.: WO2019/211414
PCT Pub. Date: Nov. 7, 2019

(65) Prior Publication Data
US 2021/0399582 A1    Dec. 23, 2021

(30) Foreign Application Priority Data
May 2, 2018  (DE) .......................... 102018206725.2

(51) Int. Cl.
*H02J 50/10* (2016.01)
*A61M 60/873* (2021.01)
(Continued)

(52) U.S. Cl.
CPC ........... *H02J 50/10* (2016.02); *A61M 60/873* (2021.01); *H02J 7/00711* (2020.01); *H02J 50/12* (2016.02); *H02J 50/90* (2016.02); *H02J 7/00034* (2020.01)

(58) Field of Classification Search
CPC .. H02J 50/10; H02J 50/90; H02J 50/12; H02J 7/00711; H02J 7/00034; A61M 60/873
(Continued)

(56) References Cited

U.S. PATENT DOCUMENTS

| 2,254,698 A | 9/1941 | Hansen, Jr. |
| 3,085,407 A | 4/1963 | Tomlinson |

(Continued)

FOREIGN PATENT DOCUMENTS

| CA | 3 000 581 | 4/2017 |
| CN | 103143072 | 6/2013 |

(Continued)

OTHER PUBLICATIONS

International Search Report for International Application No. PCT/EP2019/061320 dated Jun. 4, 2019.

(Continued)

*Primary Examiner* — Phallaka Kik
(74) *Attorney, Agent, or Firm* — Knobbe, Martens, Olson & Bear, LLP

(57) ABSTRACT

The invention firstly relates to a receiver unit (200), configured to interact for wireless energy transfer with a transmitter unit (100) separate from the receiving unit, said transmitter unit (100) comprising a primary coil ($L_1$) that can be supplied with a supply voltage ($U_V$), wherein the receiver unit (200) comprises a secondary coil ($L_2$) to which a DC link capacitor ($C_Z$) and an energy storage unit (220) are connected by a power converter (210). According to the invention, the receiver unit (200) contains a device (240) for actuating the power converter (210) when a voltage is applied on the DC link capacitor ($C_Z$) for supplying an alternating current (I) flowing through the secondary coil ($L_2$) by actuating the power converter (210) to generate an energy pulse ($E_P$). Secondly, the invention relates to a
(Continued)

transmitter unit (100) configured to interact with a receiver unit (200) separate from the transmitter unit for wireless energy transfer, wherein the transmitter unit (100) comprises a primary coil ($L_1$) that can be supplied with a supply voltage ($U_V$). There is a device (140) in the transmitter unit for detecting a voltage ($U_I$) induced in the primary coil when the supply voltage is disconnected from the primary coil ($L_1$).

19 Claims, 2 Drawing Sheets

(51) Int. Cl.
*H02J 7/00* (2006.01)
*H02J 7/34* (2006.01)
*H02J 50/12* (2016.01)
*H02J 50/90* (2016.01)

(58) Field of Classification Search
USPC ....... 320/108, 109, 104, 113, 115, 141, 142, 320/145, 155
See application file for complete search history.

(56) References Cited

U.S. PATENT DOCUMENTS

| | | |
|---|---|---|
| 3,614,181 A | 10/1971 | Meeks |
| 3,645,268 A | 2/1972 | Capote |
| 3,747,998 A | 7/1973 | Klein et al. |
| 3,790,878 A * | 2/1974 | Brokaw ............ H02M 3/33507 323/267 |
| 3,807,813 A | 4/1974 | Milligan |
| 4,441,210 A | 4/1984 | Hochmair et al. |
| 4,888,009 A | 12/1989 | Lederman et al. |
| 4,888,011 A | 12/1989 | Kung et al. |
| 4,896,754 A | 1/1990 | Carlson et al. |
| 5,000,177 A | 3/1991 | Hoffmann et al. |
| 5,195,877 A | 3/1993 | Kletschka |
| 5,289,821 A | 3/1994 | Swartz |
| 5,443,503 A | 8/1995 | Yamane |
| 5,599,173 A | 2/1997 | Chen et al. |
| 5,613,935 A | 3/1997 | Jarvik |
| 5,629,661 A | 5/1997 | Ooi et al. |
| 5,690,674 A | 11/1997 | Diaz |
| 5,713,954 A | 2/1998 | Rosenberg et al. |
| 5,766,207 A | 6/1998 | Potter et al. |
| 5,843,141 A | 12/1998 | Bischoff et al. |
| 5,888,242 A | 3/1999 | Antaki et al. |
| 6,053,873 A | 4/2000 | Govari et al. |
| 6,058,958 A | 5/2000 | Benkowski et al. |
| 6,149,405 A | 11/2000 | Abe et al. |
| 6,212,430 B1 | 4/2001 | Kung et al. |
| 6,224,540 B1 | 5/2001 | Lederman et al. |
| 6,254,359 B1 | 7/2001 | Aber |
| 6,264,601 B1 | 7/2001 | Jassawalla et al. |
| 6,324,430 B1 | 11/2001 | Zarinetchi et al. |
| 6,324,431 B1 | 11/2001 | Zarinetchi et al. |
| 6,361,292 B1 | 3/2002 | Chang et al. |
| 6,366,817 B1 | 4/2002 | Kung |
| 6,389,318 B1 | 5/2002 | Zarinetchi et al. |
| 6,398,734 B1 | 6/2002 | Cimochowski et al. |
| 6,400,991 B1 | 6/2002 | Kung |
| 6,442,434 B1 | 8/2002 | Zarinetchi et al. |
| 6,445,956 B1 | 9/2002 | Laird et al. |
| 6,471,713 B1 | 10/2002 | Vargas et al. |
| 6,496,733 B2 | 12/2002 | Zarinetchi et al. |
| 6,508,756 B1 | 1/2003 | Kung et al. |
| 6,516,227 B1 * | 2/2003 | Meadows ........ A61N 1/37247 607/46 |
| 6,527,698 B1 | 3/2003 | Kung et al. |
| 6,530,876 B1 | 3/2003 | Spence |
| 6,540,658 B1 | 4/2003 | Fasciano et al. |
| 6,553,263 B1 | 4/2003 | Meadows et al. |
| 6,561,975 B1 | 5/2003 | Pool et al. |
| 6,592,620 B1 | 7/2003 | Lancisi et al. |
| 6,979,338 B1 | 12/2005 | Loshakove et al. |
| 7,062,331 B2 | 6/2006 | Zarinetchi et al. |
| 7,070,398 B2 | 7/2006 | Olsen et al. |
| 7,155,291 B2 | 12/2006 | Zarinetchi et al. |
| 7,160,243 B2 | 1/2007 | Medvedev |
| 7,338,521 B2 | 3/2008 | Antaki et al. |
| 7,513,864 B2 | 4/2009 | Kantrowitz et al. |
| 7,520,850 B2 | 4/2009 | Brockway |
| 7,762,941 B2 | 7/2010 | Jarvik |
| 7,794,384 B2 | 9/2010 | Sugiura et al. |
| 7,819,916 B2 | 10/2010 | Yaegashi |
| 7,942,805 B2 | 5/2011 | Shambaugh, Jr. |
| 7,959,551 B2 | 6/2011 | Jarvik |
| 8,012,079 B2 | 9/2011 | Delgado, III |
| 8,075,472 B2 | 12/2011 | Zilbershlag et al. |
| 8,088,059 B2 | 1/2012 | Jarvik |
| 8,231,519 B2 | 7/2012 | Reichenbach et al. |
| 8,489,200 B2 | 7/2013 | Zarinetchi et al. |
| 8,608,635 B2 | 12/2013 | Yomtov et al. |
| 8,612,002 B2 | 12/2013 | Faltys et al. |
| 8,620,447 B2 | 12/2013 | D'Ambrosio et al. |
| 8,766,788 B2 | 7/2014 | D'Ambrosio |
| 8,827,890 B2 | 9/2014 | Lee et al. |
| 8,862,232 B2 | 10/2014 | Zarinetchi et al. |
| 8,870,739 B2 | 10/2014 | LaRose et al. |
| 8,900,114 B2 | 12/2014 | Tansley et al. |
| 8,961,389 B2 | 2/2015 | Zilbershlag |
| 9,002,468 B2 | 4/2015 | Shea et al. |
| 9,002,469 B2 | 4/2015 | D'Ambrosio |
| 9,071,182 B2 | 6/2015 | Yoshida et al. |
| 9,220,826 B2 | 12/2015 | D'Ambrosio |
| 9,283,314 B2 | 3/2016 | Prasad et al. |
| 9,381,286 B2 | 7/2016 | Spence et al. |
| 9,440,013 B2 | 9/2016 | Dowling et al. |
| 9,456,898 B2 | 10/2016 | Barnes et al. |
| 9,486,566 B2 | 11/2016 | Siess |
| 9,492,600 B2 | 11/2016 | Strueber et al. |
| 9,539,094 B2 | 1/2017 | Dale et al. |
| 9,561,362 B2 | 2/2017 | Malinowski |
| 9,569,985 B2 | 2/2017 | Alkhatib et al. |
| 9,592,397 B2 | 3/2017 | Hansen et al. |
| 9,603,984 B2 | 3/2017 | Romero et al. |
| 9,616,107 B2 | 4/2017 | VanAntwerp et al. |
| 9,713,701 B2 | 7/2017 | Sarkar et al. |
| 9,717,831 B2 | 8/2017 | Schuermann |
| 9,724,083 B2 | 8/2017 | Quadri et al. |
| 9,800,172 B1 | 10/2017 | Leabman |
| 9,833,314 B2 | 12/2017 | Corbett |
| 9,833,611 B2 | 12/2017 | Govea et al. |
| 9,848,899 B2 | 12/2017 | Sliwa et al. |
| 9,974,894 B2 | 5/2018 | Morello |
| 10,143,571 B2 | 12/2018 | Spence et al. |
| 10,463,508 B2 | 11/2019 | Spence et al. |
| 10,732,583 B2 | 8/2020 | Rudser |
| 11,000,282 B2 | 5/2021 | Schuelke et al. |
| 11,056,878 B2 | 7/2021 | Gao et al. |
| 11,065,437 B2 | 7/2021 | Aber et al. |
| 11,103,715 B2 | 8/2021 | Fort |
| 11,110,265 B2 | 9/2021 | Johnson |
| 11,179,559 B2 | 11/2021 | Hansen |
| 11,224,737 B2 | 1/2022 | Petersen et al. |
| 11,291,826 B2 | 4/2022 | Tuval et al. |
| 11,316,371 B1 * | 4/2022 | Partovi ............. G06F 1/1635 |
| 11,317,988 B2 | 5/2022 | Hansen et al. |
| 11,344,717 B2 | 5/2022 | Kallenbach et al. |
| 11,351,359 B2 | 6/2022 | Clifton et al. |
| 11,351,360 B2 | 6/2022 | Rudser et al. |
| 11,368,081 B2 | 6/2022 | Vogt et al. |
| 11,369,785 B2 | 6/2022 | Callaway et al. |
| 11,369,786 B2 | 6/2022 | Menon et al. |
| 11,389,641 B2 | 7/2022 | Nguyen et al. |
| 11,406,483 B2 | 8/2022 | Wirbisky et al. |
| 11,406,520 B2 | 8/2022 | Lam |
| 11,406,802 B2 | 8/2022 | DeGraaf et al. |
| 11,413,443 B2 | 8/2022 | Hodges et al. |
| 11,413,444 B2 | 8/2022 | Nix et al. |
| 11,439,806 B2 | 9/2022 | Kimball et al. |

(56) References Cited

U.S. PATENT DOCUMENTS

| | | |
|---|---|---|
| 11,471,692 B2 | 10/2022 | Aghassian et al. |
| 11,497,906 B2 | 11/2022 | Grace et al. |
| 11,517,737 B2 | 12/2022 | Struthers et al. |
| 11,517,738 B2 | 12/2022 | Wisniewski |
| 11,517,740 B2 | 12/2022 | Agarwa et al. |
| 11,529,508 B2 | 12/2022 | Jablonsk et al. |
| 11,583,671 B2 | 2/2023 | Nguyen et al. |
| 11,596,727 B2 | 3/2023 | Siess et al. |
| 11,602,624 B2 | 3/2023 | Siess et al. |
| 11,682,924 B2 | 6/2023 | Hansen et al. |
| 11,689,057 B2 | 6/2023 | Hansen |
| 11,699,551 B2 | 7/2023 | Diekhans et al. |
| 11,752,354 B2 | 9/2023 | Stotz et al. |
| 11,804,767 B2 | 10/2023 | Vogt et al. |
| 2001/0016686 A1 | 8/2001 | Okada et al. |
| 2002/0177324 A1 | 11/2002 | Metzler |
| 2003/0040765 A1 | 2/2003 | Breznock |
| 2003/0125766 A1 | 7/2003 | Ding |
| 2003/0130581 A1 | 7/2003 | Salo et al. |
| 2004/0167410 A1 | 8/2004 | Hettrick |
| 2005/0006083 A1 | 1/2005 | Chen et al. |
| 2005/0107847 A1 | 5/2005 | Gruber et al. |
| 2006/0004423 A1 | 1/2006 | Boveja et al. |
| 2006/0190036 A1 | 8/2006 | Wendel et al. |
| 2006/0196277 A1 | 9/2006 | Allen et al. |
| 2007/0129767 A1 | 6/2007 | Wahlstrand |
| 2007/0282209 A1 | 12/2007 | Lui et al. |
| 2008/0015481 A1 | 1/2008 | Bergin et al. |
| 2008/0079392 A1 | 4/2008 | Baarman et al. |
| 2008/0082005 A1 | 4/2008 | Stern et al. |
| 2008/0211455 A1* | 9/2008 | Park .................. H02J 50/10 320/108 |
| 2008/0266922 A1 | 10/2008 | Mumtaz et al. |
| 2009/0010462 A1 | 1/2009 | Ekchian et al. |
| 2009/0024042 A1 | 1/2009 | Nunez et al. |
| 2009/0134711 A1* | 5/2009 | Issa .................. H02J 50/12 307/104 |
| 2009/0198307 A1 | 8/2009 | Mi et al. |
| 2009/0198312 A1 | 8/2009 | Barker |
| 2009/0276016 A1 | 11/2009 | Phillips et al. |
| 2009/0312650 A1 | 12/2009 | Maile et al. |
| 2010/0191035 A1 | 7/2010 | Kang et al. |
| 2010/0219967 A1 | 9/2010 | Kaufmann |
| 2010/0280568 A1 | 11/2010 | Bulkes et al. |
| 2010/0331918 A1 | 12/2010 | Digiore et al. |
| 2011/0137394 A1 | 6/2011 | Lunsford et al. |
| 2011/0224720 A1 | 9/2011 | Kassab et al. |
| 2012/0022645 A1 | 1/2012 | Burke |
| 2012/0050931 A1 | 3/2012 | Terry et al. |
| 2012/0112543 A1* | 5/2012 | van Wageningen .... H02J 50/60 307/104 |
| 2012/0158074 A1 | 6/2012 | Hall |
| 2012/0212178 A1* | 8/2012 | Kim .................. H02J 50/10 320/108 |
| 2012/0235633 A1 | 9/2012 | Kesler et al. |
| 2013/0069651 A1 | 3/2013 | Lumiani |
| 2013/0099585 A1 | 4/2013 | Von Novak et al. |
| 2013/0116575 A1 | 5/2013 | Mickle et al. |
| 2013/0303970 A1 | 11/2013 | Keenan et al. |
| 2014/0012282 A1 | 1/2014 | Fritsch |
| 2014/0039587 A1 | 2/2014 | Romero |
| 2014/0063666 A1 | 3/2014 | Kallal et al. |
| 2014/0094645 A1 | 4/2014 | Lafontaine et al. |
| 2014/0104898 A1 | 4/2014 | Yeo et al. |
| 2014/0107754 A1 | 4/2014 | Fuhs et al. |
| 2014/0135884 A1 | 5/2014 | Tockman et al. |
| 2014/0194058 A1* | 7/2014 | Lee .................. H04B 5/0037 455/41.1 |
| 2014/0233184 A1 | 8/2014 | Thompson et al. |
| 2014/0249603 A1 | 9/2014 | Yan et al. |
| 2014/0265620 A1 | 9/2014 | Hoarau et al. |
| 2015/0028805 A1 | 1/2015 | Dearden et al. |
| 2015/0090372 A1 | 4/2015 | Branagan et al. |
| 2015/0196076 A1 | 7/2015 | Billingslea |
| 2015/0290372 A1 | 10/2015 | Muller et al. |
| 2015/0290373 A1 | 10/2015 | Rudser et al. |
| 2015/0333532 A1 | 11/2015 | Han et al. |
| 2015/0380972 A1 | 12/2015 | Fort |
| 2016/0022889 A1 | 1/2016 | Bluvshtein et al. |
| 2016/0067395 A1 | 3/2016 | Jimenez et al. |
| 2016/0081680 A1 | 3/2016 | Taylor |
| 2016/0087558 A1 | 3/2016 | Yamamoto |
| 2016/0095968 A1 | 4/2016 | Rudser |
| 2016/0175501 A1 | 6/2016 | Schuermann |
| 2016/0268846 A1 | 9/2016 | Akuzawa et al. |
| 2016/0271309 A1 | 9/2016 | Throckmorton et al. |
| 2016/0331980 A1 | 11/2016 | Strommer et al. |
| 2016/0344302 A1 | 11/2016 | Inoue |
| 2017/0047781 A1 | 2/2017 | Stanislawski et al. |
| 2017/0070082 A1 | 3/2017 | Zheng et al. |
| 2017/0136164 A1 | 5/2017 | Yeatts |
| 2017/0143977 A1 | 5/2017 | Kaib et al. |
| 2017/0202575 A1 | 7/2017 | Stanfield et al. |
| 2017/0203104 A1 | 7/2017 | Nageri et al. |
| 2017/0231717 A1 | 8/2017 | Forsell |
| 2017/0271919 A1 | 9/2017 | Von Novak, III et al. |
| 2017/0275799 A1 | 9/2017 | Chen |
| 2017/0288448 A1 | 10/2017 | Kranz et al. |
| 2017/0303375 A1* | 10/2017 | Woodhead ............... H05C 1/04 |
| 2017/0353053 A1 | 12/2017 | Muratov |
| 2017/0354812 A1 | 12/2017 | Callaghan et al. |
| 2018/0078329 A1 | 3/2018 | Hansen et al. |
| 2018/0194236 A1* | 7/2018 | Elshaer .................. B60L 53/12 |
| 2018/0207336 A1 | 7/2018 | Solem |
| 2018/0256796 A1 | 9/2018 | Hansen |
| 2018/0256800 A1 | 9/2018 | Conyers et al. |
| 2018/0280708 A1 | 10/2018 | Escalona et al. |
| 2019/0004037 A1 | 1/2019 | Zhang et al. |
| 2019/0060543 A1 | 2/2019 | Khanal et al. |
| 2019/0068004 A1 | 2/2019 | Louis |
| 2019/0097447 A1 | 3/2019 | Partovi |
| 2019/0175808 A1 | 6/2019 | Zilbershlag et al. |
| 2019/0222064 A1 | 7/2019 | Du et al. |
| 2019/0344000 A1 | 11/2019 | Kushwaha et al. |
| 2019/0351120 A1 | 11/2019 | Kushwaha et al. |
| 2019/0393735 A1 | 12/2019 | Lee et al. |
| 2020/0054806 A1 | 2/2020 | Sun |
| 2020/0139032 A1 | 5/2020 | Bryson et al. |
| 2020/0227954 A1 | 7/2020 | Ding et al. |
| 2020/0350812 A1 | 11/2020 | Vogt et al. |
| 2021/0052793 A1 | 2/2021 | Struthers et al. |
| 2021/0057804 A1 | 2/2021 | Wenning |
| 2021/0143688 A1 | 5/2021 | Agrawal et al. |
| 2021/0290931 A1 | 9/2021 | Baumbach |
| 2021/0322011 A1 | 10/2021 | Schuelke et al. |
| 2021/0336484 A1 | 10/2021 | Araujo et al. |
| 2021/0351628 A1 | 11/2021 | Araujo et al. |
| 2021/0379360 A1 | 12/2021 | Schellenberg |
| 2021/0386990 A1 | 12/2021 | Stotz et al. |
| 2021/0393944 A1 | 12/2021 | Wenning |
| 2022/0080184 A1 | 3/2022 | Clifton et al. |
| 2022/0080185 A1 | 3/2022 | Clifton et al. |
| 2022/0320901 A1 | 10/2022 | Araujo et al. |
| 2023/0191141 A1 | 6/2023 | Wenning et al. |
| 2023/0352236 A1 | 11/2023 | Diekhans et al. |
| 2023/0381526 A1 | 11/2023 | Stotz et al. |

FOREIGN PATENT DOCUMENTS

| | | |
|---|---|---|
| CN | 103 942 511 A | 7/2014 |
| CN | 104274873 | 1/2015 |
| CN | 104888293 | 3/2017 |
| CN | 106 776 441 | 5/2017 |
| DE | 103 02 550 | 8/2004 |
| DE | 10 2012 200 912 | 7/2013 |
| DE | 11 2012 005 944 | 12/2014 |
| DE | 10 2016 106 683 | 10/2016 |
| DE | 10 2018 206 758 | 11/2019 |
| EP | 0 930 086 | 7/1999 |
| EP | 2454799 A2 | 5/2012 |
| EP | 2 752 209 | 7/2014 |
| EP | 2 782 210 | 9/2014 |
| EP | 2 859 911 | 4/2015 |

(56) References Cited

FOREIGN PATENT DOCUMENTS

| | | | |
|---|---|---|---|
| EP | 2 966 753 | 1/2016 | |
| EP | 2 709 689 | 4/2017 | |
| EP | 3 220 505 | 9/2017 | |
| EP | 3 357 523 | 1/2021 | |
| EP | 3 423 126 | 2/2021 | |
| EP | 3 490 628 | 2/2021 | |
| EP | 3 198 677 | 3/2021 | |
| EP | 3 248 647 | 3/2021 | |
| EP | 3 436 106 | 3/2021 | |
| EP | 3 509 661 | 3/2021 | |
| EP | 3 528 863 | 3/2021 | |
| EP | 3 436 105 | 4/2021 | |
| EP | 3 116 407 | 5/2021 | |
| EP | 3 131 600 | 6/2021 | |
| EP | 2 608 731 | 7/2021 | |
| EP | 2 599 510 | 10/2021 | |
| EP | 3 077 018 | 10/2021 | |
| EP | 3 485 936 | 10/2021 | |
| EP | 3 539 613 | 2/2022 | |
| EP | 2 858 718 | 3/2022 | |
| EP | 3 624 867 | 3/2022 | |
| EP | 3 755 237 | 4/2022 | |
| EP | 3 497 775 | 7/2022 | |
| EP | 3 711 788 | 8/2022 | |
| EP | 2 654 883 | 9/2022 | |
| EP | 3 485 819 | 9/2022 | |
| EP | 3 600 477 | 10/2022 | |
| EP | 3 808 408 | 11/2022 | |
| EP | 3 858 422 | 11/2022 | |
| EP | 2 892 583 | 1/2023 | |
| EP | 3 597 231 | 1/2023 | |
| EP | 3 856 275 | 1/2023 | |
| EP | 3 003 420 | 2/2023 | |
| EP | 3 946 511 | 4/2023 | |
| EP | 3 826 104 | 5/2023 | |
| JP | H11178249 A * | 7/1999 | ............ H01F 38/14 |
| JP | 2013-013216 | 1/2013 | |
| JP | 2018-046708 | 3/2018 | |
| KR | 1185112 B1 * | 9/2012 | ........... A61N 1/3787 |
| WO | WO 2008/106103 | 9/2008 | |
| WO | WO 2009/023905 A1 | 2/2009 | |
| WO | WO 2009/029977 | 3/2009 | |
| WO | WO 2010/042054 A1 | 4/2010 | |
| WO | WO 2011/007300 | 1/2011 | |
| WO | WO 2012/147061 | 11/2012 | |
| WO | WO-2013164831 A1 * | 11/2013 | ........... A61N 1/3787 |
| WO | WO 2015/152732 | 10/2015 | |
| WO | WO 2017/021846 | 2/2017 | |
| WO | WO 2017/060257 | 4/2017 | |
| WO | WO 2017/066257 | 4/2017 | |
| WO | WO 2017/089440 | 6/2017 | |
| WO | WO 2017/118738 | 7/2017 | |
| WO | WO 2017/165372 | 9/2017 | |
| WO | WO 2017/218349 | 12/2017 | |
| WO | WO 2018/033799 | 2/2018 | |
| WO | WO 2018/100192 | 6/2018 | |
| WO | WO 2019/025258 | 2/2019 | |
| WO | WO 2019/025259 | 2/2019 | |
| WO | WO 2019/025260 | 2/2019 | |
| WO | WO 2019/101786 | 5/2019 | |
| WO | WO 2019/145253 | 8/2019 | |
| WO | WO 2019/158996 | 8/2019 | |
| WO | WO 2019/183247 | 9/2019 | |
| WO | WO 2019/185511 | 10/2019 | |
| WO | WO 2019/185512 | 10/2019 | |
| WO | WO 2019/211400 | 11/2019 | |
| WO | WO 2019/211405 | 11/2019 | |
| WO | WO 2019/211410 | 11/2019 | |
| WO | WO 2019/211413 | 11/2019 | |
| WO | WO 2019/211414 | 11/2019 | |
| WO | WO 2019/211415 | 11/2019 | |
| WO | WO 2019/211416 | 11/2019 | |
| WO | WO 2019/229224 | 12/2019 | |
| WO | WO 2019/234151 | 12/2019 | |
| WO | WO 2019/241556 | 12/2019 | |
| WO | WO 2019/244031 | 12/2019 | |
| WO | WO 2020/089429 | 5/2020 | |
| WO | WO 2023/076869 | 5/2023 | |

OTHER PUBLICATIONS

International Preliminary Report on Patentability and Written Opinion received in PCT/EP2019/061320, dated Aug. 4, 2020 in 19 pages.

Atkinson et al., "Pulse-Doppler Ultrasound and Its Clinical Application", The Yale Journal of Biology and Medicine, 1977, vol. 50, pp. 367-373.

Leguy et al., "Assessment of Blood Volume Flow in Slightly Curved Arteries from a Single Velocity Profile", Journal of Biomechanics, 2009, pp. 1664-1672.

Sinha et al., "Effect of Mechanical Assistance of the Systemic Ventricle in Single Ventricle Circulation with Cavopulmonary Connection", The Journal of Throacic and Cardiovascular Surgery, Apr. 2014, vol. 147, No. 4, pp. 1271-1275.

Vieli, A., "Doppler Flow Determination", BJA: British Journal of Anaesthesia, 1988, vol. 60, pp. 107S-112S.

* cited by examiner

RECEIVING UNIT, TRANSMISSION UNIT, POWER TRANSMISSION SYSTEM AND METHOD FOR WIRELESS POWER TRANSMISSION

BACKGROUND

Field

The present invention relates to a receiver unit, a transmitter unit, an energy transfer system with such a receiver unit and such a transmitter unit, and a method for wireless energy transfer.

Description of the Related Art

A wireless, in particular inductive, energy transfer can be used for the energy supply of loads and in particular for charging energy storage devices. This type of energy transfer can generate a magnetic field in a transmitter unit with a primary coil, said magnetic field inducing a voltage and thus a current flow in a receiver unit with a secondary coil.

A decisive point for an optimal and efficient energy transfer in such an energy transfer system is usually that the transmitter unit and the receiver unit are positioned as optimally as possible relative to one another. This relates in particular to the coils present therein. In case of insufficiently precise positioning, the energy transfer is generally not efficient, because the voltage induced in the secondary coil is too low. Due to legally mandated limits and regulations for electromagnetic fields, it must be ensured that the transmitter unit only starts with the energy transfer and generates an alternating field when it is placed on a receiver unit, i.e. correctly positioned.

For example, an energy transfer system for wireless energy transfer is known from CN 103 942 511 A, wherein infrared or wireless technology are proposed for better positioning. WO 2009/023905 A1 proposes, for example, the use of magnets to better position the transmitter unit relative to the receiver unit. It is known from CN 106 776 441 A that NFC chips (NFC is the English abbreviation for "Near Field Communication") are used for this purpose. U.S. Pat. No. 6,212,430 B1 proposes free positioning using a coil arrangement.

SUMMARY

The object of the invention is to provide a positioning assistance function to a receiver unit configured to interact for purposes of wireless energy transfer with a transmitter unit separate from the receiver unit.

In particular, it is an object of the invention to simplify the correct positioning of a transmitter unit for the inductive transfer of electrical energy to a receiver unit arranged in the body of a person.

This object is achieved by a receiver unit and a method for wireless energy transfer described herein. Advantageous embodiments of the invention are described herein.

One idea of the invention is that the transmitter unit is informed at what point in time it is correctly placed or positioned and the energy transfer can be started and at what point in time a transmission of fields is not permitted.

A problem with the identification of the transmitter unit arises in particular in the case of so-called transcutaneous energy transfer, wherein the receiver unit is arranged or implanted under the skin in a human body. Such transcutaneous energy transfer is advantageous, for example, for cardiovascular or cardiac support systems (so-called VAD systems, from English "Ventricular Assist Device"), because there is then no permanent wound in the skin through which a cable is guided. The implantation of the receiver unit under the skin means that the receiver unit is not visible and is usually not detectable or only difficult to detect, which makes it difficult to optimally position the transmitter unit.

There is also the possibility that the extracorporeal transmitter unit will be briefly removed. During such a period, the extracorporeal transmitter unit should not emit any electromagnetic fields, because metallic objects in the immediate environment could otherwise heat up against regulation. The transmitter unit therefore requires information about its current spatial positioning.

The invention is based upon an energy transfer system for wireless energy transfer with a transmitter unit and a receiver unit separate from the transmitter unit or based upon such a transmitter unit and such a receiver unit. In particular, the receiver unit is thus configured to interact for wireless energy transfer with a transmitter unit separate from the receiver unit. The transmitter unit comprises a primary coil that can be supplied with a predetermined supply voltage. For this purpose, an inverter, for example with suitable semiconductor switches, is generally also specified in order to generate an oscillation of the voltage in the primary coil with a supply voltage present as a direct current voltage. A magnetic alternating field can thus be generated by means of the transmitter unit.

The receiver unit correspondingly comprises a secondary coil, to which a DC link capacitor or generally a DC link capacitance is connected using a power converter that can be operated as a rectifier and inverter. The power converter can in particular be an active rectifier, for example with suitable semiconductor switches. The DC link capacitor, which is charged during energy transfer, is used in particular for smoothing the alternating current that is induced in the secondary coil and then rectified. As mentioned above, this type of wireless energy transfer is an inductive energy transfer.

An energy storage device—for example a storage battery or a rechargeable battery—that can be or should be charged by means of wireless or inductive energy transfer is then connected to the power converter. In addition, a load can also be connected to the power converter, said load being supplied with voltage and thus with energy using the DC link voltage present on the DC link or on the DC link capacitor.

According to the invention, the receiver unit is configured to actuate the power converter such that the secondary coil generates an energy pulse when the energy storage device supplies a voltage to the DC link capacitor.

The generated energy pulse can also be understood as an energy impulse. The energy pulse is created when a current pulse or current impulse sent through the secondary coil results in a coil magnetic field that changes as a function of time.

Furthermore, according to the invention, it is specified that the transmitter unit is configured to detect a voltage induced in the primary coil when the primary coil is disconnected from the supply voltage—this can be achieved by the energy pulse generated in the secondary coil of the receiver unit—and, based thereupon, to perform at least one predetermined function. The at least one predetermined function comprises, in particular, the application of the supply voltage to the primary coil and the actuation of the primary coil for wireless energy transfer, and thus in particular preferably automatically starting a charging process of the energy storage device.

The efficiency or effectiveness of the energy transfer from the transmitter unit to the receiver unit is determined by the so-called coupling factor. The coupling factor is a metric for the magnetic interaction between the primary coil and the secondary coil, which in particular also depends on the positioning of the two coils relative to one another. The higher the coupling factor, the better or more efficient the energy transfer.

The invention now makes use of the fact that the direction of the energy transfer in an energy transfer system with a transmitter unit and a receiver unit can occur not only from the transmitter unit to the receiver unit, but also vice-versa from the receiver unit to the transmitter unit. For this purpose, a sufficient supply voltage is then required in the receiver unit, which can be ensured by the energy storage device. Likewise, the power converter must be actuated accordingly, i.e. in the sense of an inverter, so that an alternating magnetic field and thus an energy pulse can be at least briefly generated in the secondary coil.

This energy pulse can then be detected or identified in the transmitter unit by means of the primary coil. There should be no voltage supplied to the primary coil for this purpose, so that any present capacitor is not charged. The inverter is then used or actuated as a rectifier.

In this way, it can therefore be determined whether the transmitter unit is positioned sufficiently precisely relative to the receiver unit, because otherwise the energy pulse could not be detected or at least not sufficiently well. In this context, it is also particularly expedient for the transmitter unit to be configured in order to apply the supply voltage to the primary coil and to actuate the primary coil for wireless energy transfer when a value of the voltage induced in the primary coil or a metric derived therefrom, for example the mentioned coupling factor, exceeds or falls below a predetermined threshold value (depending on how the metric or threshold value is defined).

In this way, the charging process can thus be started, in particular automatically or in an automated fashion, when the transmitter unit is positioned sufficiently precisely relative to the receiver unit. In this context, it is also expedient for a signal, for example an acoustic signal, to be emitted when the threshold value has not yet been exceeded, but, for example, a low energy pulse has already been detected. A user can thus, for example, recognize that the transmitter unit needs to be repositioned.

The receiver unit is preferably configured so that the energy pulse is generated repeatedly, in particular at predetermined time intervals. In particular, the energy pulse can be generated repeatedly until a charging process of the energy storage device carried out by the transmitter unit is detected.

It is thus possible, for example, to enable a repositioning of the transmitter unit on the receiver unit when the transmitter unit has been temporarily removed further away from the receiver unit, as can be the case, for example, for an energy transfer system for transcutaneous energy transfer when showering. In addition, it can then in particular be ensured that the transmitter unit only starts with the energy transfer when it detects an energy pulse and is thus correctly placed or positioned on the receiver unit and does not send out uncontrolled fields in the unplaced state. In other words, the transmitter unit is therefore configured to not (or not yet) actuate the primary coil for wireless energy transfer when (or as long as) the value of the voltage induced in the primary coil or the metric derived therefrom does not exceed or fall below the predetermined threshold value (depending on the definition of the metric and threshold value).

Although the proposed transmitter unit and the proposed receiver unit are advantageous for any type of wireless or inductive energy transfer, is it nevertheless particularly expedient for the receiver unit to be configured to be arranged, in particular implanted, underneath the skin in a human or animal body and/or for the transmitter unit to be designed to be arranged on the skin outside of a human or animal body. The energy transfer system thus serves the aforementioned purpose of transcutaneous energy transfer. Here, the aforementioned advantages are particularly clearly relevant, because—as mentioned—positioning the receiver unit under the skin is particularly difficult.

The subject matter of the invention is furthermore an energy transfer system for wireless energy transfer with a transmitter unit according to the invention and a receiver unit according to the invention.

With regard to the advantages as well as further preferred embodiments of the energy transfer system and in order to avoid repetitions, reference is made to the above discussion regarding the transmitter unit and the receiver unit, which applies here accordingly.

The subject matter of the invention is also a method for wireless energy transfer by means of an energy transfer system according to the invention. After the transmitter unit has been initially positioned relative to the receiver unit, an energy transfer is started when an energy pulse generated by the receiver unit induces a voltage in the primary coil of the transmitter unit and when a value of the voltage induced in the primary coil or a metric derived therefrom, for example the mentioned coupling factor, exceeds or falls below a predetermined threshold value. It should be noted in this regard that a reverse transfer function applies when the power flow is reversed, i.e. the voltage on the DC link capacitor is inversely proportional to the coupling factor and proportional to the input voltage. When the detected input voltage is low, the resulting coupling factor is large, thus resulting in a good placement or positioning.

In particular, when the value of the voltage induced in the primary coil of the transmitter unit or the metric derived therefrom does not exceed or fall below the threshold value, this allows the user of the energy transfer system to repeatedly reposition the transmitter unit until the value of the voltage induced in the primary coil of the transmitter unit or the value derived therefrom exceeds or falls below the threshold value.

This constitutes a particularly simple and fast possibility for a user of the energy transfer system to position the transmitter unit relative to the receiver unit, so that the energy transfer can be started.

Disclosed herein is an energy transfer system for wireless energy transfer with a transmitter unit and with a receiver unit separate therefrom, wherein the transmitter unit has a primary coil that can be supplied with a supply voltage, and a device for detecting a voltage induced in the primary coil when the supply voltage is disconnected from the primary coil, wherein the receiver unit has a secondary coil, to which a DC link capacitor and an energy storage unit are connected by a power converter, and also has a device designed to control the power converter when a voltage is applied by the energy storage unit to the DC link capacitor such that a current flowing through the secondary coil is provided for generating an energy pulse, said secondary coil causing the induced voltage in the primary coil, wherein the device for detecting a voltage induced in the primary coil when the supply voltage is disconnected from the primary coil ($L_1$) is used to control an inverter that applies the supply voltage to the primary coil for the wireless transfer of energy from the primary coil when a value of the voltage induced in the primary coil or a value derived therefrom exceeds or falls below a predetermined threshold value, said inverter preventing the wireless transfer of energy from the primary coil when the value of the voltage induced in the primary coil or the value derived therefrom does not exceed or fall below the specified threshold value.

Disclosed herein is a method for wireless energy transfer from a transmitter unit to a receiver unit separate therefrom, wherein energy pulses are generated in succession by means of the receiver unit, wherein a generated energy pulse induces a voltage in a primary coil of the transmitter unit, wherein the transmitter unit wirelessly transfers energy to the receiver unit when a value of the voltage induced in the primary coil or a value derived therefrom exceeds or falls below a predetermined threshold value, and wherein the wireless transfer of energy from the primary coil is prevented when the value of the voltage induced in the primary coil or the value derived therefrom does not exceed or fall below the specified threshold value.

BRIEF DESCRIPTION OF THE DRAWINGS

Further features and embodiments of the invention are disclosed in the following description and the enclosed drawing.

The invention is shown schematically based on an exemplary embodiment in the drawing and is described below with reference to the drawing.

The figures show:

Figure 1:
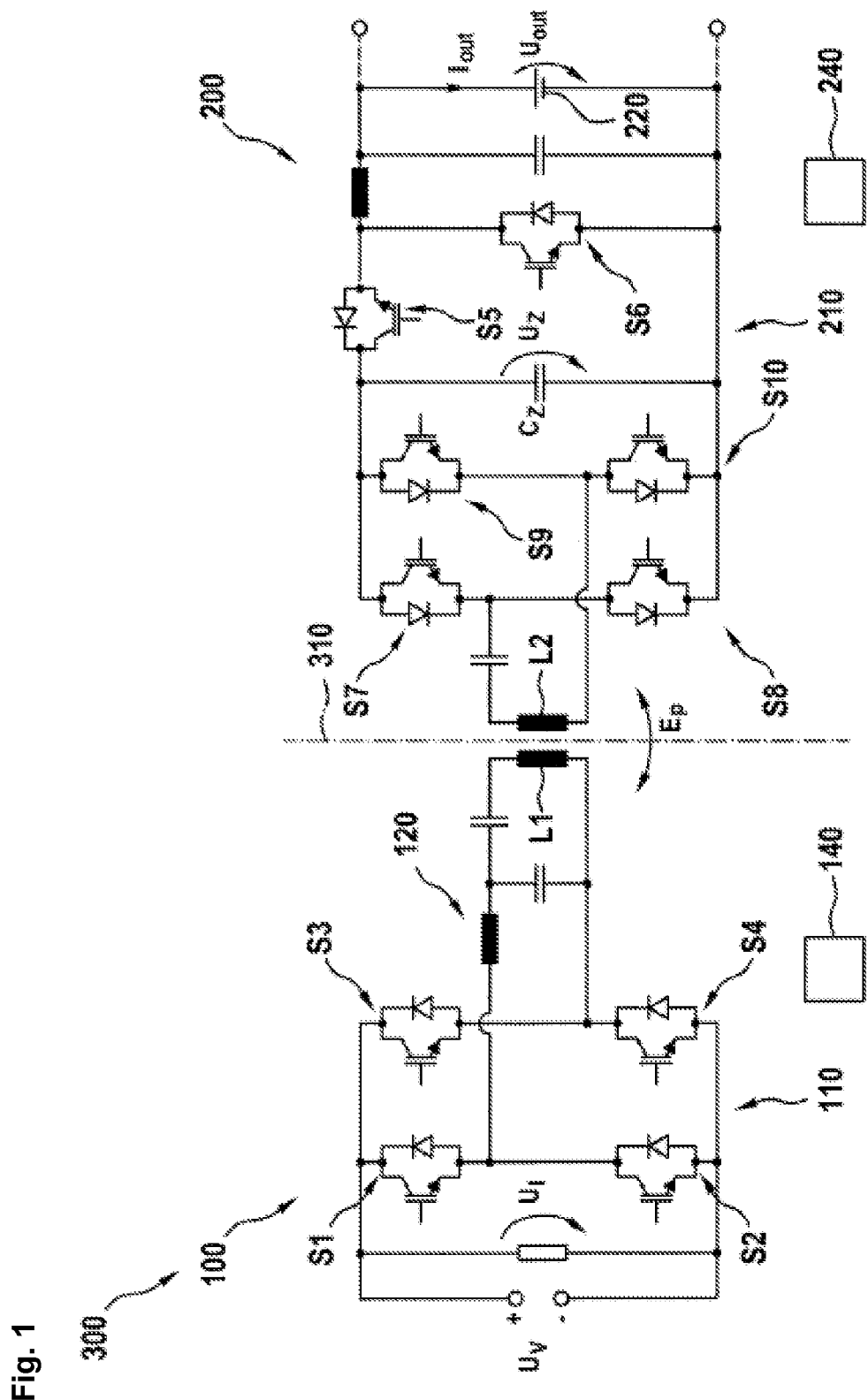
Figure 2:
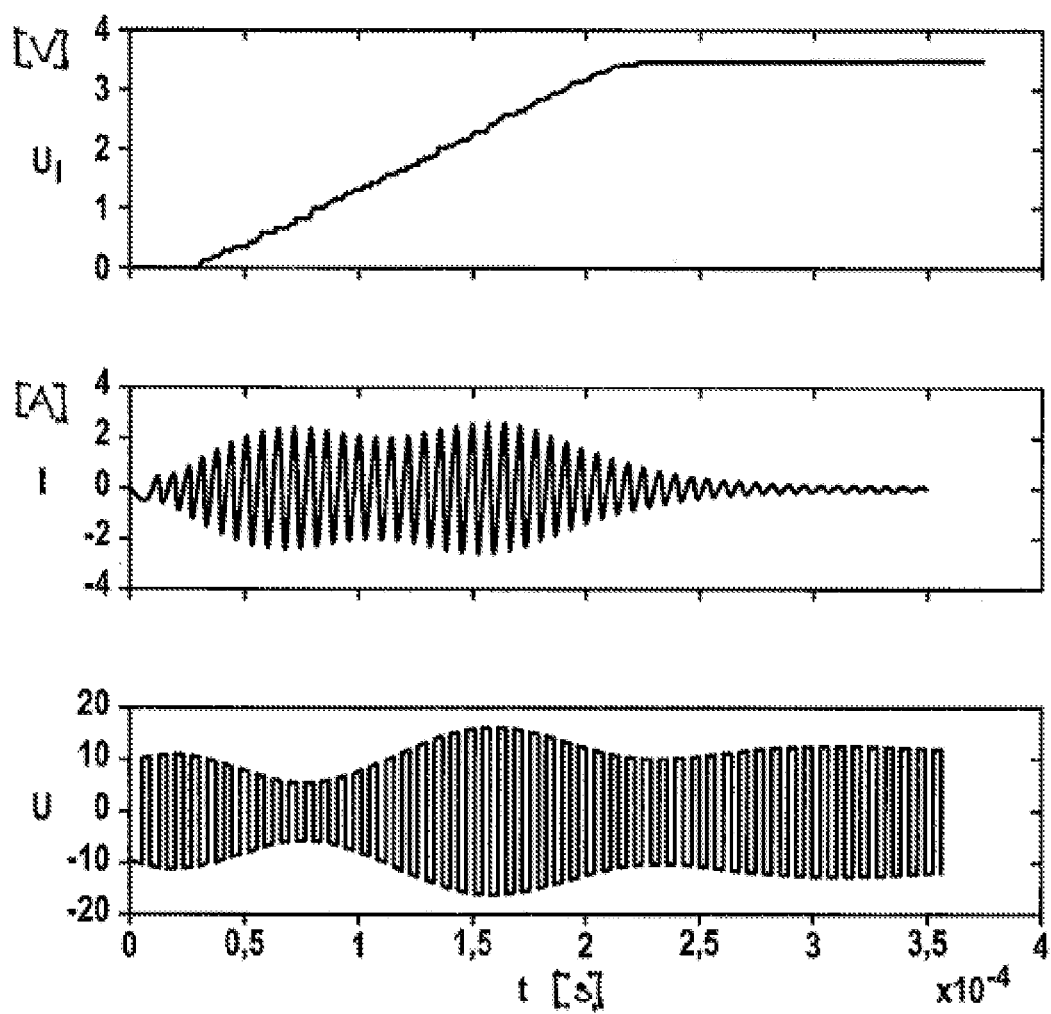

FIG. 1 a schematic representation of a transmitter unit and a receiver unit in an energy transfer system; and FIG. 2 a schematic representation of voltage and current profiles during operation of the energy transfer system.

DETAILED DESCRIPTION

FIG. 1 shows a schematic representation of an energy transfer system 300 according to the invention for wireless energy transfer in a preferred embodiment. The energy transfer system has a transmitter unit 100 and a receiver unit 200 separated therefrom, each according to a preferred embodiment of the invention.

The transmitter unit 100 comprises a primary coil $L_1$, to which an inverter 110 can supply a voltage $U_V$, said inverter having four semiconductor switches, for example MOSFETs or bipolar transistors, designated as $S_1$ to $S_4$. In addition, a pre-filter 120 and a compensation capacitance with unspecified components are arranged between the inverter 110 and the primary coil $L_1$. The compensation capacitance is used for resonant actuation (actuation with the design frequency) as reactive power compensation.

When the voltage $U_V$ is applied and the inverter is suitably actuated, an alternating magnetic field can thus be generated by means of the coil $L_1$.

The receiver unit 200 has a secondary coil $L_2$ with compensation capacitance, to which a DC link capacitor $C_Z$ is connected by a power converter 210. In turn, an energy storage unit 220 is connected to the DC link capacitor $C_Z$ by means of two semi-conductor switches $S_5$ and $S_6$, which can for example be configured as MOSFETs or bipolar transistors, and together with an inductance and a capacitance act as a buck converter, in particular. A load can be connected, for example, on the indicated connections. An output voltage $U_{out}$ with an output current $I_{out}$ can be set on the energy storage unit, for example by using the mentioned buck converter.

The power converter 210 is designed as an active rectifier with four semiconductor switches, for example MOSFETs or bipolar transistors, designated as $S_1$ to $S_4$. The energy storage unit 220 can be a storage battery or a rechargeable battery, in particular.

The receiver unit 200 can now in particular be configured to be arranged or implanted underneath the skin indicated here as 310, and for example used for a cardiac or ventricular support system. In particular, the energy storage unit 220 can be used for the energy supply of such a cardiac or ventricular support system.

With the transmitter unit 100 positioned correspondingly outside or on the skin 310, and assuming corresponding positioning, a coupling is achieved between the primary coil $L_1$ of the transmitter unit 100 and the secondary coil $L_2$ of the receiver unit 200.

If the transmitter unit is now actuated or operated in such a way that an alternating magnetic field is generated by means of the primary coil $L_1$, the coupling induces a voltage or current flow in the secondary coil $L_2$. This, in turn, causes the DC link capacitor $C_Z$ to be charged.

In the context of the present invention, the receiver unit 200 is now configured to actuate the power converter 210 embodied as an active rectifier with voltage $U_Z$ applied on the DC link capacitor by the energy storage unit 220 such that an energy pulse, schematically indicated here as $E_P$, is generated by means of the secondary coil $L_2$. The power converter 210 configured as an active rectifier is thus actuated in particular in the sense of an inverter. However, it is also conceivable to actuate the power converter 210 configured as an active rectifier by applying only a short voltage pulse with a rising flank to the secondary coil $L_2$ in order to generate a rising magnetic field.

A computing unit 240 integrated in the receiver unit 200 can be used, for example, for this actuation of the power converter 210 configured as an active rectifier. The computing unit 240 then forms a device designed to actuate the power converter 210 with a voltage applied by the energy storage unit 220 to the DC link capacitor $C_Z$, such that an AC current I flowing through the secondary coil $L_2$ is provided to generate an energy pulse $E_P$.

In the context of the present invention, the transmitter unit 100 is configured to detect a voltage $U_I$ induced in the primary coil when the primary coil $L_1$ is disconnected from the supply voltage $U_V$. This induced voltage $U_I$ is in this case, for example, tapped across a resistor. A suitable voltage measuring device can also be used for this purpose, which can for example be provided in the computing unit 140 shown and integrated into the transfer unit 100.

However, it is also conceivable that the induced voltage is not, as shown, tapped after the rectification of the voltage or energy pulse induced in the primary coil $L_1$, but rather is tapped or detected prior thereto. A suitable voltage measuring device can also be used for this purpose, which can for example be provided in the computing unit 140 shown and integrated in the transmitter unit 100.

The computing unit 140 thus forms a device for detecting a voltage $U_I$ induced in the primary coil when a supply voltage is disconnected from the primary coil $L_1$.

If the value of the induced voltage $U_I$ is then below a predetermined threshold value, it can be assumed that the two coils $L_1$ and $L_2$ are positioned sufficiently precisely to one another and the charging process of the energy storage unit 220 can be started. For this purpose, the supply voltage $U_V$ can then again first be applied to the primary coil $L_1$, and the active rectifier 210 can again be operated as a rectifier in the receiver unit 200.

The computing unit 140 integrated into the transmitter unit 100 causes a predetermined function to be carried out due to the induced voltage $U_I$ detected in the primary coil $L_1$ when a supply voltage is disconnected, said function consisting of the application of the supply voltage $U_V$ to the primary coil $L_1$ and the actuation of the primary coil $L_1$ for wireless energy transfer.

The inverter 110 is then actuated by means of the computing unit 140 such that the supply voltage $U_V$ is applied to the primary coil $L_1$ and a current flow is generated in the primary coil $L_1$ for wireless energy transfer when a value of the voltage $U_I$ induced in the primary coil or a metric derived therefrom exceeds or falls below a predetermined threshold value.

The computing unit 140 is thus a device that serves to perform a predetermined function due to the induced voltage $U_I$ detected in the primary coil $L_1$ when the supply voltage is disconnected.

FIG. 2 schematically shows voltage and current graphs when using an energy transfer system according to a preferred embodiment of the invention. For this purpose, the upper diagram shows in V the voltage $U_I$ induced in the transmitter unit, the middle diagram shows a current I in A in the oscillating circuit formed in the receiver unit with the secondary coil $L_2$, and the bottom diagram shows the associated voltage U in V applied to this oscillating circuit and corresponding to this current I, each plotted over time t in s.

It can be seen here that a voltage in the primary coil can be induced by a suitable actuation of the receiver unit 200 or the secondary coil $L_2$ and the energy pulse $E_P$ generated therewith, with which, for example, a capacitor connected to the primary coil (which can be, for example, connected in parallel to the supply voltage) is charged.

Such an energy pulse can then for example be repeatedly generated at predetermined time intervals of, for example, 30 s, and, as soon as a sufficient value of the induced voltage is measured by the transmitter unit, the transmitter unit can transition into the regular operating mode for energy transfer.

The duration of such an energy pulse can be selected very briefly, for example at most one second, so that it can be ensured that no undesirable heating occurs of metallic objects located in the vicinity.

It is conceivable, for example, that the transmitter unit is repositioned relative to the receiver unit until the induced voltage reaches the predetermined threshold value and/or until the charging process starts automatically or in an automated fashion. Furthermore, it can be determined that a positioning test has been carried out and another positioning method can alternatively be used. In this case, the power pulse only serves as a start signal for the transmitter unit.

In addition, it is thus made possible that the charging process can start automatically or in an automated fashion strictly by positioning the transmitter unit and in particular without further intervention, because the transmitter unit is given a start signal by the energy pulse.

In summary, the following preferred features of the invention should be noted, in particular:

The invention firstly relates to a receiver unit 200 configured to interact for wireless energy transfer with a transmitter unit 100 separate from the receiver unit, said transmitter unit 100 having a primary coil $L_1$ that can be supplied with a supply voltage $U_V$, wherein the receiver unit 200 has a secondary coil $L_2$ to which a DC link capacitor $C_Z$ and an energy storage unit 220 are connected by a power converter 210. The receiver unit 200 contains a device 240 for actuating the power converter 210 with a voltage applied to the DC link capacitor $C_Z$ for supplying an AC current I flowing through the secondary coil $L_2$ by actuating the power converter 210 in order to thereby generate an energy pulse $E_P$.

Secondly, the invention relates to a transmitter unit 100 configured to interact for wireless energy transfer with a receiver unit 200 separate from the transmitter unit, wherein the transmitter unit 100 comprises a primary coil $L_1$ that can be supplied with a supply voltage $U_V$. There is a device 140 in the transmitter unit for detecting a voltage $U_I$ induced in the primary coil when the supply voltage is disconnected from the primary coil $L_1$.

The invention relates, in particular, to the aspects specified in the following clauses:

1. Receiver unit (200), configured to interact for wireless energy transfer with a transmitter unit (100) separate from the receiving unit, said transmitter unit (100) comprising a primary coil ($L_1$) that can be supplied with a supply voltage ($U_V$), wherein the receiver unit (200) comprises a secondary coil ($L_2$) to which a DC link capacitor ($C_Z$) and an energy storage unit (220) are connected by a power converter (210),
   characterized in that
   the receiver unit (200) is configured to actuate the power converter (210) when voltage is applied by the energy storage unit (220) to the DC link capacitor ($C_Z$) such that an energy pulse ($E_P$) is generated by means of the secondary coil ($L_2$).
2. Receiver unit (200) according to clause 1, wherein the power converter (210) is configured as an active rectifier.
3. Receiver unit (200) according to clause 1 or 2 configured to generate the energy pulse ($E_P$) repeatedly, in particular at predetermined time intervals.
4. Receiver unit (200) according to clause 3, configured to repeatedly generate the energy pulse ($E_P$) until a charging process of the energy storage unit (220) carried out by the transmitter unit (100) is detected.
5. Receiver unit (200) according to any of the above clauses, designed to be arranged underneath the skin (310) in a human or animal body.
6. Transmitter unit (100) configured to interact for wireless energy transfer with a receiver unit (200) separate from the transmitter unit,
   wherein the transmitter unit (100) comprises a primary coil ($L_1$) that can be supplied with a supply voltage ($U_V$),
   characterized in that
   the transmitter unit (100) is configured to detect a voltage ($U_I$) induced in the primary coil when a primary coil ($L_1$) is disconnected from the supply voltage and to perform at least one predetermined function based thereon.
7. Transmitter unit (100) according to clause 6, wherein the at least one predetermined function comprises the application of the supply voltage ($U_V$) to the primary coil ($L_1$) and the actuation of the primary coil ($L_1$) for wireless energy transfer.
8. Transmitter unit (100) according to clause 6 or 7, configured to apply the supply voltage ($U_V$) to the primary coil ($L_1$) and to actuate the primary coil ($L_1$) for wireless energy transfer when a value of the voltage (U$_I$) induced in the primary coil or a metric derived therefrom exceeds or falls below a predetermined threshold value.

9. Transmitter unit (100) according to clause 8, configured to not actuate the primary coil (L$_1$) for wireless energy transfer when the value of the voltage induced in the primary coil (U$_I$) or the metric derived therefrom does not exceed or does not fall below the predetermined threshold value.

10. Transmitter unit (100) according to any of the clauses 6 to 9, designed to be arranged on the skin (310) outside of a human or animal body.

11. Energy transfer system (300) for wireless energy transfer with a transmitter unit (100) according to any of clauses 6 to 10 and a receiver unit (200) separate therefrom according to any of clauses 1 to 5.

12. Method for wireless energy transfer by means of an energy transfer system (300) according to clause 11, wherein an energy transfer is started automatically when an energy pulse (E$_P$) generated by means of the receiver unit (200) in the primary coil (L$_1$) of the transmitter unit (100) induces a voltage, and when a value of the voltage (U$_I$) induced in the primary coil or a metric derived therefrom exceeds or falls below a predetermined threshold value.

LIST OF REFERENCE SYMBOLS

100 Transmitter unit
110 Inverter
120 Pre-filter
140 Computing unit
200 Receiver unit
210 Power converter/rectifier
220 Energy storage unit/Energy storage
240 Computing unit
300 Energy transfer system
310 Skin
C$_{cz}$ DC link capacitor
E$_P$ Energy pulse
I Current
I$_{out}$ Output current
L$_1$ Primary coil
L$_2$ Secondary coil
S$_1$ to S$_6$ Semiconductor switch
t Time
U Voltage
U$_{out}$ Output voltage
U$_I$ Induced voltage
U$_V$ Supply voltage
U$_Z$ Voltage

The invention claimed is:

1. A system for wireless power transmission, the system comprising:
a transmitter unit comprising a primary coil and a voltage detecting device, the primary coil configured to be supplied with a supply voltage, and the voltage detecting device configured to detect an induced voltage in the primary coil when the primary coil is disconnected from the supply voltage; and
a receiver unit comprising a secondary coil and a processor, the secondary coil connected to a DC link capacitor and an energy storage unit via a power converter, and the processor configured to control the power converter when a voltage is applied by the energy storage unit to the DC link capacitor such that a current flowing through the secondary coil is configured to generate an energy pulse, wherein the energy pulse causes the induced voltage in the primary coil,
wherein the voltage detecting device is configured to control an inverter configured to apply the supply voltage to the primary coil for the wireless power transmission from the primary coil when a value of the induced voltage in the primary coil or a value derived therefrom satisfies a predetermined condition,
wherein the inverter is configured to prevent the wireless power transmission from the primary coil when the value of the voltage induced in the primary coil or the value derived therefrom does not satisfy the predetermined condition, and
wherein the processor of the receiver unit is configured to repeatedly generate the energy pulse via the power converter until a charging process of the energy storage unit by the transmitter unit is detected.

2. The system of claim 1, wherein the power converter is an active rectifier.

3. The system of claim 1, wherein the receiver unit is configured to be positioned underneath a skin.

4. The system of claim 1, wherein the transmitter unit is configured to be positioned on a skin.

5. The system of claim 1, wherein the processor of the receiver unit is configured to repeatedly generate the energy pulse periodically at a predetermined time interval.

6. The system of claim 5, wherein the predetermined time interval is 30 seconds.

7. The system of claim 1, wherein a duration of the energy pulse does not exceed one second.

8. A method for wireless power transmission, the method comprising:
detecting energy pulses generated at a receiver unit, wherein the energy pulses cause an induced voltage in a primary coil of a transmitter unit;
determining a value of the induced voltage at the primary coil;
determining that the value of the induced voltage at the primary coil satisfies a predetermined condition; and
wirelessly transmitting power to the receiver unit,
wherein the receiver unit is configured to repeatedly generate the energy pulses until a charging process of an energy storage unit of the receiver unit is detected.

9. The method of claim 8, wherein the receiver unit is configured to repeatedly generate the energy pulses at a predetermined time interval.

10. The method of claim 9, wherein the predetermined time interval is 30 seconds.

11. The method of claim 8, wherein a duration of each of the energy pulses does not exceed one second.

12. The method of claim 8, wherein the transmitter unit is configured to be positioned proximate to the receiver unit until the induced voltage reaches a threshold value.

13. The method of claim 8, wherein the transmitter unit is configured to be positioned proximate to the receiver unit until the transmitter unit transfers energy wirelessly to the receiver unit.

14. The method of claim 8 further comprising:
detecting proximal positioning of the receiver unit relative to the transmitter unit.

15. A system for wireless power transmission, the system comprising:
a transmitter unit comprising an inverter and a primary coil configured to be supplied with a supply voltage; and
a receiver unit comprising a secondary coil and an energy storage unit, the energy storage unit configured to cause a current flowing through the secondary coil and repeatedly generate an energy pulse until a charging process of the energy storage unit is detected, the energy pulse configured to cause an induced voltage in the primary coil, wherein when a value of the induced voltage in the primary coil satisfies a predetermined condition, the inverter of the transmitter unit is configured to apply the supply voltage to the primary coil for wireless power transmission between the transmitter unit and the receiver unit.

16. The system of claim 15, wherein when the value of the induced voltage in the primary coil does not satisfy the predetermined condition, the inverter prevents the wireless power transmission between the transmitter unit and the receiver unit.

17. The system of claim 15, wherein the energy storage unit is configured to generate the energy pulse at a predetermined interval.

18. The system of claim 17, wherein the predetermined interval is 30 seconds.

19. The system of claim 17, wherein a duration of the energy pulse does not exceed one second.

\* \* \* \* \*